(12) United States Patent
Gao et al.

(10) Patent No.: US 9,828,307 B2
(45) Date of Patent: Nov. 28, 2017

(54) METHOD FOR PRODUCING ISOPROPYL BENZENE FROM BENZENE AND PROPYLENE

(71) Applicants: China Petroleum & Chemical Corporation, Beijing (CN); Shanghai Research Institute of Petrochemical Technology SINOPEC, Shanghai (CN)

(72) Inventors: Huanxin Gao, Shanghai (CN); Hongyuan Zong, Shanghai (CN); Yilun Wei, Shanghai (CN); Hui Yao, Shanghai (CN); Ruifang Gu, Shanghai (CN); Hua Fang, Shanghai (CN); Shufang Ji, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(*) Notice: Subject to any disclaimer, the term of this patent is extended or adjusted under 35 U.S.C. 154(b) by 294 days.

(21) Appl. No.: 14/525,857

(22) Filed: Oct. 28, 2014

(65) Prior Publication Data
US 2015/0119619 A1  Apr. 30, 2015

(30) Foreign Application Priority Data

Oct. 28, 2013 (CN) .......................... 2013 1 0512503
Oct. 28, 2013 (CN) .......................... 2013 1 0512683

(51) Int. Cl.
*C07C 2/66* (2006.01)

(52) U.S. Cl.
CPC ............ *C07C 2/66* (2013.01); *C07C 2529/70* (2013.01); *Y02P 20/52* (2015.11)

(58) Field of Classification Search
CPC ........... C07C 2/66; C07C 15/085; C07C 2/68; C07C 2/54
See application file for complete search history.

(56) References Cited

U.S. PATENT DOCUMENTS 2,382,318 A    8/1945  Ipatieff et al.
5,817,908 A *  10/1998 Mehlberg ................. C07C 2/54
                                                            585/716
(Continued)

FOREIGN PATENT DOCUMENTS

CN    1228073 A    9/1999
CN    1235146 A    11/1999
(Continued)

OTHER PUBLICATIONS

Office Action dated Dec. 2, 2015, by the State Intellectual Property Office of China in corresponding Chinese Application No. 201310512503.2. (5 pages).
(Continued)

*Primary Examiner* — Brian McCaig
*Assistant Examiner* — Jason Chong
(74) *Attorney, Agent, or Firm* — Buchanan Ingersoll & Rooney PC

(57) ABSTRACT

A method for producing isopropyl benzene includes the following steps. Step A: feeding a first stream containing benzene and a first stream containing propylene into a first reaction zone to contact a first catalyst for alkylation, and obtaining a first stream containing isopropyl benzene from the first reaction zone, dividing the first stream containing isopropyl benzene into a stream Ia and a stream IIa, the stream Ia circulating back into the first reaction zone and the stream IIa entering into a second reaction zone, having the stream entering the second reaction zone to contact a second catalyst for alkylation, and obtaining a second stream containing isopropyl benzene from the second reaction zone,
(Continued)

and purifying at least a partial stream IIIa of the second stream containing isopropyl benzene, and obtaining a product isopropyl benzene.

16 Claims, 2 Drawing Sheets

(56) References Cited

U.S. PATENT DOCUMENTS

| | | | |
|---|---|---|---|
| 6,008,422 A * | 12/1999 | Schulz | C07C 2/66 585/449 |
| 6,297,417 B1 | 10/2001 | Samson et al. | |
| 6,479,721 B1 | 11/2002 | Gajda | |
| 6,835,862 B1 | 12/2004 | Gajda et al. | |
| 7,501,547 B2 | 3/2009 | Clark et al. | |
| 2005/0075237 A1 * | 4/2005 | Kelly | B01J 29/7057 502/49 |
| 2008/0194895 A1 * | 8/2008 | Sohn | C07C 2/66 585/435 |
| 2013/0237733 A1 * | 9/2013 | Majumder | C07C 2/66 585/323 |

FOREIGN PATENT DOCUMENTS

| | | |
|---|---|---|
| CN | 1314589 C | 5/2007 |
| CN | 101466815 A | 6/2009 |
| CN | 100554156 C | 10/2009 |
| CN | 102464566 A | 5/2012 |
| GB | 1592592 | 7/1981 |

OTHER PUBLICATIONS

Office Action dated Dec. 2, 2015, by the State Intellectual Property Office of China in corresponding Chinese Application No. 201310512683.4. (7 pages).

Extended European Search Report dated Mar. 16, 2015 in corresponding EP Application No. 14190441.7.

* cited by examiner

METHOD FOR PRODUCING ISOPROPYL BENZENE FROM BENZENE AND PROPYLENE

TECHNICAL FIELD

The present invention relates to the technical field of chemical process. Specifically, it relates to a method for producing isopropyl benzene.

TECHNICAL BACKGROUND

Isopropyl benzene, also known as cumene, is a bulky chemical intermediate for manufacturing phenol, acetone, and α-methyl styrene. In the industry, isopropyl benzene is produced by the alkylation of benzene with propylene. The main byproduct of the alkylation is poly-isopropyl benzene. Early in 1945, the UOP Company has published a method (SPA method) for producing isopropyl benzene from propylene and benzene under the presence of acid catalyst (U.S. Pat. No. 2,382,318). SPA process uses solid phosphoric acid as the alkylation catalyst. Because solid phosphoric acid cannot catalyze transalkylation, the SPA process does not comprise transalkylation unit. Therefore, the SPA process can only run under relative high molar ratio of benzene to propylene (in a range of 5~7), also the yield of isopropyl benzene is less than 95%. In the 1980s, the Monsanto Company developed the technique for manufacturing isopropyl benzene under the presence of the alkylation catalyst $AlCl_3$ and realized the industrial application thereof. Because $AlCl_3$ cannot catalyze transalkylation either, the yield of isopropyl benzene from $AlCl_3$ method is still low. Moreover, $AlCl_3$ itself can cause severe pollution and corrosion.

In the 1990s, companies including Dow, CD Tech, Mobil-Badger, Enichem and UOP successively disclosed the fixed bed process using microporous zeolite as catalysts, which is capable of transalkylation. In the prior art, benzene and propylene first react in an alkylation reactor, producing isopropyl benzene and poly-isopropyl benzene; and after being separated in a rectification system, the poly-isopropyl benzene mixes with benzene and the mixture is fed into a transalkylation reactor with a single catalyst bed for transalkylation.

In the existing technology for producing isopropyl benzene, the alkylation of benzene with propylene usually occurs in a single fixed bed reactor comprising a plurality of stages, applying technologies including staged feeding of propylene and external circulation of reaction liquid. The benzene to propylene ratio is usually larger than 2.0. In fact, the benzene to propylene ratio in most cumene factory is larger than 3.0. When benzene to propylene ratio is to be further reduced to 2.0 or lower, it encounters rapid deactivation of the catalyst (caused by high concentration of propylene), or insufficient propylene conversion (caused by excessive external circulation), or much impurity n-propyl benzene in the product (caused by over high reaction temperature). The above technical obstacles restrict the further reduction of benzene to propylene ratio. U.S. Pat. No. 6,835,862B1 discloses an optimization process using relatively high external circulation volume of reaction liquid to reduce the deactivation rate of the catalyst. However, with the process of a single reactor, high external recycle ratio cannot solve the above three contradictory problems simultaneously.

SUMMARY OF THE INVENTION

The present invention provides a new method for producing isopropyl benzene from benzene and propylene so as to solve the problems of high benzene to propylene ratio and low propylene conversion rate in the prior art. The method according to the present invention can also reduce the deactivation rate of the catalyst. Moreover, with the present invention, it is not necessary to shut down the entire reaction system in order to replace the deactivated catalyst, thereby realizing continuous operation of the process.

According to the present invention, a method for producing isopropyl benzene is provided, comprising:

step A: feeding a first stream containing benzene and a first stream containing propylene into a first reaction zone to contact a first catalyst for alkylation, and obtaining a first stream containing isopropyl benzene from the first reaction zone, dividing the first stream containing isopropyl benzene into a stream Ia and a stream IIa, the stream Ia circulating back into the first reaction zone and the stream IIa entering into a second reaction zone, having the stream entering the second reaction zone to contact a second catalyst for alkylation, and obtaining a second stream containing isopropyl benzene from the second reaction zone, and purifying at least a partial stream IIIa of the second stream containing isopropyl benzene, and obtaining a product isopropyl benzene.

In an embodiment of the method according to the present invention, the method comprises step A: circulating a partial stream IVa of the second stream containing isopropyl benzene to the second reaction zone, a recycle ratio of the first reaction zone being larger than that of the second reaction zone. When there is no stream from the second stream containing isopropyl benzene circulating to the second reaction zone, i.e., the recycle ratio of the second reaction zone is 0, the recycle ratio of the first reaction zone is still larger than that of the second reaction zone. In step A, the first reaction zone is the primary reaction zone and the second reaction zone is the secondary reaction zone. Therefore, the recycle ratio of the primary reaction zone is larger than that of the secondary reaction zone. In an embodiment of said method, in step A, the ratio of the recycle ratio of the second reaction zone to that of the first reaction zone is 0~0.5, preferably 0.01~0.5.

The method according to the present invention arranges at least two reaction zones, so that the stream flowing out of the primary reaction zone can enter into at least one secondary reaction zone for further reaction. The primary reaction zone operates under a relatively high recycle ratio, and the secondary reaction zone operates under a relatively low recycle ratio or with barely any externally circulating material. This essentially extends the total residence time and improves the propylene conversion rate. The temperatures in the primary and secondary reaction zones can be adjusted separately such that the propylene can be completely converted and the content of impurities can be low. By means of the method according to the present invention, the benzene to propylene ratio (the molar ratio of benzene to propylene) can be lower than 2.0, the propylene conversion rate can be over 99.99%, and the content of n-propyl benzene in the product can be less than 200 mg in 1 kg isopropyl benzene. Better technical effect is thus achieved.

In the present invention, the stream containing isopropyl benzene flowing out of the first reaction zone is called the first stream containing isopropyl benzene and the stream containing isopropyl benzene flowing out of the second reaction zone is called the second stream containing isopropyl benzene. The stream circulating back to the reaction zone can continue to react and further generate isopropyl benzene.

According to an embodiment of the present invention, in step A, the operating conditions in the first reaction zone comprise: a molar ratio of the benzene in the first stream containing benzene to the propylene in the first stream containing propylene being 0.5:1~3.0:1, a weight hourly space velocity of the first stream containing propylene calculated by propylene being 0.1~10 hr$^{-1}$, a reaction temperature being 90~180° C., a reaction pressure being 1.0~4.0 MPa, and a recycle ratio being 1~50. Preferably, the operating conditions in the first reaction zone comprise: the molar ratio of the benzene in the first stream containing benzene to the propylene in the first stream containing propylene being 1.0:1~3.0:1, the weight hourly space velocity of the first stream containing propylene calculated by propylene being 0.2~5.0 hr$^{-1}$, the reaction temperature being 95~150° C., the reaction pressure being 2.0~3.0 MPa, and the recycle ratio being 2~25.

According to another embodiment of the present invention, in step A, the operating conditions in the second reaction zone comprises: a reaction temperature being 80~160° C., a reaction pressure being 1.0~4.0 MPa, and a liquid phase weight hourly space velocity being 1~100 hr$^{-1}$. Preferably, the operating conditions in the second reaction zone comprises: the reaction temperature being 90~150° C., the reaction pressure being 2.0~3.0 MPa, and the liquid phase weight hourly space velocity being 1~60 hr$^{-1}$.

According to another embodiment of the method of the present invention, in step A, the recycle ratio of the second reaction zone is 0.1~15, preferably 0.1~10.

According to an embodiment of the method of the present invention, the method further comprises, in step A, feeding the second stream containing benzene and/or a second stream containing propylene into the second reaction zone so as to achieve better reaction effect. In an embodiment, the weight hourly space velocity of the second stream containing benzene calculated by benzene is 0.5~30 hr$^{-1}$, and/or the weight hourly space velocity of the second stream containing propylene calculated by propylene is 0.1~5 hr$^{-1}$.

According to a preferred embodiment of the present invention, the stream containing benzene (including the first and/or the second stream containing benzene) is benzene and the stream containing propylene (including the first and/or the second stream containing propylene) is propylene.

According to another embodiment of the method of the present invention, the first catalyst and/or the second catalyst is/are selected from a group consisting of Beta zeolite, mordenite, and zeolite having MWW stratified structure. The first catalyst and the second catalyst can be the same or different. The catalyst used in the present invention is selected from a group consisting of Beta zeolite, mordenite, and zeolite having MWW stratified structure. The zeolite having MWW stratified structure can be selected from a group consisting of MCM-22, MCM-56, MCM-49 and zeolite having MWW structure as disclosed in literatures CN200410066636.2 and CN200610029980.3.

In the method according to the present invention, preferably, the first reaction zone and the second reaction zone each comprises a reactor having at least one stage, or a reaction zone having at least two single stage reactors in series connection, or a reaction zone having at least one single stage reactor and at least one reactor comprising at least two stages in series connection.

In an embodiment of said method, the first stream containing propylene enters into the primary reaction zone by stages. The first stream containing propylene can also be fed to the first reaction zone in batches, so that excessive local concentration of propylene can be avoided. In another embodiment of the method, the second stream containing propylene enters into the secondary reaction zone by stages. The propylene can also be fed to the secondary reaction zone in batches.

According another embodiment of the method, in step A, the first stream containing benzene enters into the first reaction zone from the top thereof and the stream Ia circulates back to the first reaction zone from the top thereof.

According to another embodiment, in step A, the stream entering the second reaction zone enters into the second reaction zone from the top thereof.

In the method according to the present invention, the pressure refers to a gage pressure. The recycle ratio refers to the weight ratio of the stream in the stream flowing out of the reaction zone which circulates back to the reaction zone to the stream therein which does not circulate back to the reaction zone.

In order to solve the three contradictory problems of rapid deactivation of the catalyst, insufficient propylene conversion rate, and high content of impurity n-propyl benzene in the product, the method according to the present invention arranges at least two reaction zones, so that the stream flowing out of the primary reaction zone can enter into at least one secondary reaction zone for further reaction. The primary reaction zone operates under a relatively high recycle ratio, and the secondary reaction zone operates under a relatively low recycle ratio or with barely any externally circulating material. This essentially extends the total residence time. The propylene almost completely reacts in the first reaction zone. A small amount of unreacted propylene continues to react in the second reaction zone, thereby guaranteeing a high propylene conversion rate. In the prior art, the reaction temperature for alkylation is usually about 150° C., the adjustment range for the reaction temperature is within 10° C., or even smaller than 5° C. Temperature change can severely influence the propylene conversion rate and the content of n-propyl benzene. In the present invention, by arranging a primary reaction zone and a secondary reaction zone and allowing the temperatures therein to be changed separately, full conversion of propylene and low content of impurity can be guaranteed. By means of the method according to the present invention, the benzene to propylene ratio can be lower than 2.0, the propylene conversion rate can be over 99.99%, and the n-propyl benzene in the product can be less than 200 mg in 1 kg isopropyl benzene. Better technical effect is thus obtained.

According to a preferred embodiment of the present invention, the first reaction zone comprises a plurality of reactors in parallel connection. When the activity of the catalyst in one of the reactors decreases or lost, it can be recovered in the reactor separately without having to shut down the operation of the entire reaction system. According to another preferred embodiment of the present invention, the second reaction zone comprises a plurality of reactors in parallel connection. When the activity of the catalyst in one of the reactors decreases or lost, it can be recovered in the reactor separately without having to shut down the operation of the entire reaction system. By means of such arrangements, switching operation of the reaction zones and process combination can be realized, thereby improving the operational stability of the reaction zones.

According to another embodiment of the present invention, the method further comprises:

switching from step A to a step B when the activity of the first catalyst in the first reaction zone drops below a preset value, wherein step B comprises:

turning off the first stream containing benzene and the first stream containing propylene, feeding only the second stream containing benzene and the second stream containing propylene into the second reaction zone to contact the second catalyst for alkylation, and obtaining the second stream containing isopropyl benzene, and dividing the second isopropyl stream containing benzene into a stream IIIa and a stream IVa, the stream IVa circulating back to the second reaction zone and the stream IIIa being purified, obtaining the product isopropyl benzene, the first catalyst at this moment being in an activity recovery phase;

Switching from step B to a step C after the activity of the first catalyst recovers, wherein step C comprises:

feeding the second stream containing benzene and the second stream containing propylene into the second reaction zone to contact the second catalyst for alkylation, and obtaining the second stream containing isopropyl benzene, dividing the second stream containing isopropyl benzene into a stream IIIb and a stream IVb, the stream IVb circulating back to the second reaction zone and the stream IIIb entering the first reaction zone, having the stream entering the first reaction zone to contact the first catalyst for alkylation, and obtaining the first stream containing isopropyl benzene, and purifying at least a partial stream IIb of the first stream containing isopropyl benzene and obtaining the product isopropyl benzene;

Switching from step C to a step D when the activity of the second catalyst in the second reaction zone drops below a preset value, wherein step D comprises:

turning off the second stream containing benzene and the second stream containing propylene, feeding only the first stream containing benzene and the first stream containing propylene into the first reaction zone to contact the first catalyst for alkylation, obtaining the first stream containing isopropyl benzene, and dividing the first stream containing isopropyl benzene into a stream IIb and a stream Ib, the stream Ib circulating back to the first reaction zone and the stream IIb being purified, obtaining the product isopropyl benzene, the second catalyst at this moment being at an activity recovery phase; and Switching from step D to step A after the activity of the second catalyst recovers. That is, the present invention provides a method for continuously preparing isopropyl benzene, comprising:

step A: feeding a first stream containing benzene and a first stream containing propylene into a first reaction zone to contact a first catalyst for alkylation, and obtaining a first stream containing isopropyl benzene from the first reaction zone, dividing the first stream containing isopropyl benzene into a stream Ia and a stream IIa, the stream Ia circulating back into the first reaction zone and the stream IIa entering a second reaction zone, having the stream entering the second reaction zone to contact a second catalyst for alkylation, and obtaining a second stream containing isopropyl benzene from the second reaction zone, and purifying at least a partial stream IIIa of the second stream containing isopropyl benzene, and obtaining a product isopropyl benzene.

Switching from step A to a step B when the activity of the first catalyst in the first reaction zone drops below a preset value, wherein step B comprises:

turning off the first stream containing benzene and the first stream containing propylene, feeding only the second stream containing benzene and the second stream containing propylene into the second reaction zone to contact the second catalyst for alkylation, and obtaining the second stream containing isopropyl benzene, and dividing the second stream containing isopropyl benzene into a stream IIIa and a stream IVa, the stream IVa circulating back to the second reaction zone and the stream IIIa being purified, obtaining the product isopropyl benzene, the first catalyst at this moment is in an activity recovery phase;

Switching from step B to a step C after the activity of the first catalyst recovers, wherein step C comprises:

feeding the second stream containing benzene and the second stream containing propylene into the second reaction zone to contact the second catalyst for alkylation, and obtaining the second stream containing isopropyl benzene, dividing the second stream containing isopropyl benzene into a stream IIIb and a stream IVb, the stream IVb circulating back to the second reaction zone and the stream IIIb entering the first reaction zone, having the stream entering the first reaction zone to contact the first catalyst for alkylation, and obtaining the first stream containing isopropyl benzene, and purifying at least a partial stream IIb of the first stream containing isopropyl benzene and obtaining the product isopropyl benzene;

Switching from step C to a step D when the activity of the second catalyst in the second reaction zone drops below a preset value, wherein step D comprises:

turning off the second stream containing benzene and the second stream containing propylene, feeding only the first stream containing benzene and the first stream containing propylene into the first reaction zone to contact the first catalyst for alkylation, obtaining the first stream containing isopropyl benzene, and dividing the first stream containing isopropyl benzene into a stream IIb and a stream Ib, the stream Ib circulating back to the first reaction zone and the stream IIb being purified, obtaining the product isopropyl benzene, the second catalyst at this moment being at an activity recovery phase; and Switching from step D to step A after the activity of the second catalyst recovers.

The definition of step A in the method for continuously producing isopropyl benzene is as mentioned above.

According to the present invention, the activity of the catalyst would decrease as the reaction proceeds for a long time. Because in step A, the first reaction zone is the primary reaction zone, the first catalyst therein would lose activity first. In an embodiment, the catalyst activity being lower than a preset value means that the activity of the catalyst decreases or lost. The activity of the catalyst can be characterized by the conversion rate of the raw material. In an embodiment, when the conversion rate of the raw material is lower than 99.95%, such as 99.91%, it can be concluded that the activity of the catalyst has dropped below the preset value.

In step B, after the first stream containing benzene and the first stream containing propylene are turned off, there is no stream flowing through the first reaction zone, or no reaction is occurring in the first reaction zone. Reaction only occurs in the second reaction zone, and the entire reaction system is in a single reaction zone operating mode. At this time, the first catalyst in the first reaction zone is in an activity recovery phase. The catalyst activity can be recovered through off-line recovery, or by directly replacing the catalyst with fresh new first catalyst.

After the activity of the first catalyst in the first reaction zone is recovered, i.e., the regeneration or replacement of deactivated catalyst is completed, the reaction switches from step B to step C. The single-reaction zone operating mode is switched to two-reaction zone operating mode. In step C, the second reaction zone is the primary reaction zone and the first reaction zone is the secondary reaction zone.

In an embodiment of the method according to the present invention, in step C, a partial stream Ib of the first stream containing isopropyl benzene circulates to the first reaction zone, the recycle ratio of the second reaction zone being larger than that of the first reaction zone. In step C, when there is no stream from the first stream containing isopropyl benzene circulating to the first reaction zone, i.e., the recycle ratio of the first reaction zone is 0, the recycle ratio of the second reaction zone is still larger than that of the first reaction zone. The recycle ratio of the primary reaction zone is larger than that of the secondary reaction zone. In a preferred embodiment, in step C, the ratio of the recycle ratio of the first reaction zone to that of the second reaction zone is in a range of 0~0.5, preferably 0.01~0.5.

In another embodiment of the method according to the present invention, in step C, the operating conditions of the second reaction zone comprises a molar ratio of the benzene in the second stream containing benzene to the propylene in the second stream containing propylene of 0.5:1~3.0:1, a weight hourly space velocity of the second stream containing propylene calculated by propylene of 0.1~10 hr$^{-1}$, a reaction temperature of 90~180° C., a reaction pressure of 1.0~4.0 MPa, and a recycle ratio of 1~50. Preferably, the molar ratio of the benzene in the second stream containing benzene to the propylene in the second stream containing propylene is 1.0:1~3.0:1, the weight hourly space velocity of the second stream containing propylene calculated by propylene is 0.2~5.0 hr$^{-1}$, the reaction temperature is 95~150° C., the reaction pressure is 2.0~3.0 MPa, and the recycle ratio is 2~25.

In another embodiment of the method of the present invention, in step C, the operating conditions in the first reaction zone comprises a reaction temperature of 80~160° C., a reaction pressure of 1.0~4.0 MPa, and a liquid phase weight hourly space velocity of 1~100 hr$^{-1}$. Preferably, the reaction temperature is 90~150° C., the reaction pressure is 2.0~3.0 MPa, and the liquid phase weight hourly space velocity is 1~60 hr$^{-1}$.

In another embodiment of the method according to the present invention, in step C, the recycle ratio of the first reaction zone is 0.1~15, preferably 0.1~10.

Through steps A to C of said method, two reaction zones are arranged such that a wide range of temperature adjustment can be realized, thereby lowering the content of n-propyl benzene in the product and improving the propylene conversion rate. In the meantime, switching operations between two reaction zones and process combination can be realized and the operational stability can be improved. The temperature in each reaction zone can be adjusted in a range of 90~180° C. such that full conversion of propylene and low content of impurity can be guaranteed. Based on the condition of the catalysts in the reaction zones, the reaction operation can switch between the reaction zones, the catalyst can be regenerated on-line in the reaction zones, and even only one reaction zone can be put into operation. The method of the present invention does not require the entire reaction apparatus to shut down when replacing the catalyst. The content of n-propyl benzene can be less than 300 mg in 1 kg isopropyl benzene and the propylene conversion rate can be over 99.99%. Better technical effect is thus obtained.

In another embodiment of the method, in step C, the first stream containing benzene and the first stream containing propylene are let into the first reaction zone so as to achieve better technical effect. The weight hourly space velocity of the first stream containing benzene calculated by benzene is 0.5~30 hr$^{-1}$, and the weight hourly space velocity of the first stream containing propylene calculated by propylene is 0.1~5 hr$^{-1}$.

According to the present invention, in step C, the second reaction zone is the primary reaction and the first reaction zone is the secondary reaction zone. As the reaction proceeds for a long time period, the activity of the second catalyst in the second reaction zone decreases. When the activity of the second catalyst which is characterized by a propylene conversion rate decreases, the reaction switches from step C to step D.

In step D, the second stream containing benzene and the second stream containing propylene are turned off. Thus, there is no stream passing through the second reaction zone, or there is no reaction occurring in the second reaction zone. Reaction occurs only in the first reaction zone, i.e., only a single reaction zone is in operation in the entire system. At this moment, the second catalyst in the second reaction zone is in an activity recovery phase. The activity of the catalyst can be recovered through off-line regeneration, or by directly replacing the catalyst with new second catalyst.

According to the present invention, in steps B and D, only a single reaction zone is in operation. The technological parameters of steps B and D can be obtained with reference to the existing technology which is well known to one skilled in the art, thus will not be explained in details herein.

When the second catalyst in the second reaction zone recovers activity, the reaction switches from step D to step A. As the reaction proceeds from step D to step A, switch operations between reaction zones are realized. When the activity of the second catalyst recovers, the single-reaction zone operating mode is switched to two-reaction zone operating mode.

According to another embodiment of the present invention, the method of the present invention comprises steps A to D in switching operations, forming a set of steps for continuously producing isopropyl benzene. According to the method of the present invention, even when the catalyst needs to be replaced or regenerated after a long time of operation, it is not necessary to shut down the entire reaction apparatus. Further, the content of n-propyl benzene can be less than 200 mg in 1 kg isopropyl benzene and the propylene conversion rate can be over 99.99%. Better technical effect is thus obtained.

According to the present invention, in the prior art, in order to reduce the content of n-propyl benzene in the product, the technical means of lowering reaction temperature in the reaction zone and high external recycle ratio are adopted. However, low temperature and high recycle ratio certainly would cause the propylene conversion rate to decrease. To solve this problem, the present invention arranges a primary reaction zone and a secondary reaction zone (the reaction zone with higher recycle ratio is the primary reaction zone and the reaction zone with lower recycle ratio (including 0) is the secondary reaction zone). The primary reaction zone operates under a relatively high external recycle ratio, and the secondary reaction zone operates under relatively low recycle ratio or with barely any externally circulating material presented. In step A, the propylene almost completely reacts in the first reaction zone (primary reaction zone), and the stream flowing out of the first reaction zone barely enters into the second reaction zone (secondary reaction zone) in which there is barely any circulating stream for further reaction. The above process actually extends the residence time, so that the small amount of unreacted propylene in the first reaction zone continues to react, thereby guaranteeing a high propylene conversion rate. When the reaction first begins, the first reaction zone is the primary reaction zone and the second reaction zone is the secondary reaction zone. When the activity of the catalyst in the first reaction zone decreases or lost, the reaction zones switch places, and the reaction proceeds to step C, i.e., the first reaction zone becomes the secondary reaction zone and the second reaction zone becomes the primary reaction zone, thereby realizing stable production process. By using a combination of at least two reaction zones, the method of the present invention allows for a relatively wide range of temperature adjustment, thereby lowering the content of n-propyl benzene and improving the propylene conversion rate. In the meantime, switching operations between the reaction zones and process combination can be achieved and the operational stability of the apparatus can be improved.

According to the present invention, the temperature of alkylation in the prior art is usually around 150° C., the adjustment range of the temperature is within 10° C., or even smaller than 5° C. Temperature change would severely influence the propylene conversion rate and the content of the impurity n-propyl benzene. The present invention arranges a primary reaction zone and a secondary reaction zone and allows the temperatures in the primary reaction zone and the secondary reaction zone to be adjusted separately. The temperature in each of the reaction zones, in particular the primary reaction zone, can be adjusted in a range of 90~180° C. Thus full conversion of propylene and low impurity content can be guaranteed.

According to the present invention, based on the condition of the catalysts, the reaction can switch between reaction zones and the catalysts can be regenerated in the reaction zones. And it can even be realized that only one reaction zone is in operation while the catalyst in the other reaction zone is regenerated on-line. Thus, interruption to the technological process can be avoided and continuous production of isopropyl benzene can be realized. Therefore, the present invention has high economic and social value.

By combining two reaction zones according to the present invention, isopropyl benzene can be produced with high efficiency, even under low benzene to propylene ratio. The propylene conversion rate can be above 99.99%. The deactivation rate of the catalyst can be reduced without having to shut down the reaction process, thereby realizing continuous operation. The economic and social benefit of the present invention is profound.

DETAILED DESCRIPTION OF THE EMBODIMENTS

The present invention will be explained in details with reference to the embodiments and the accompanying drawings.

Figure 1:
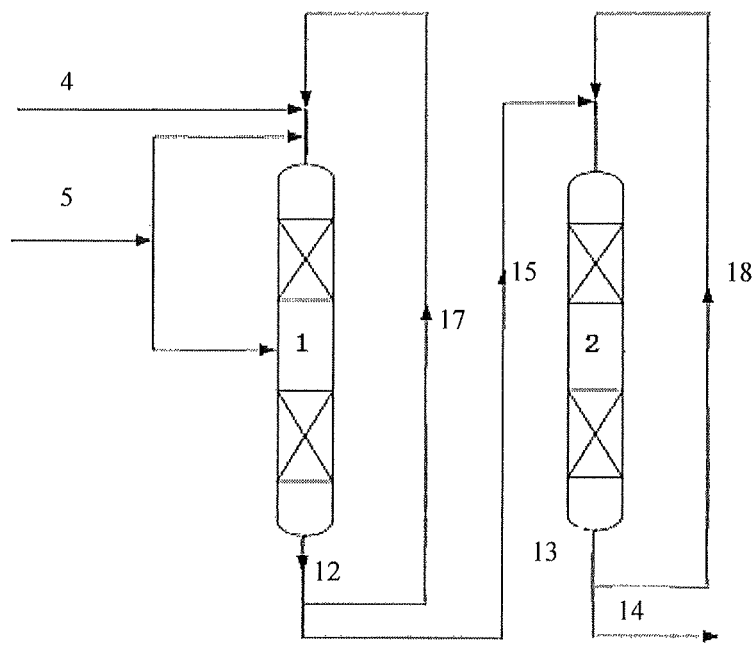
FIG. 1 schematically shows a technological process of an Example of the present invention,
FIG. 2 schematically shows a technological process in the prior art.
Figure 2:
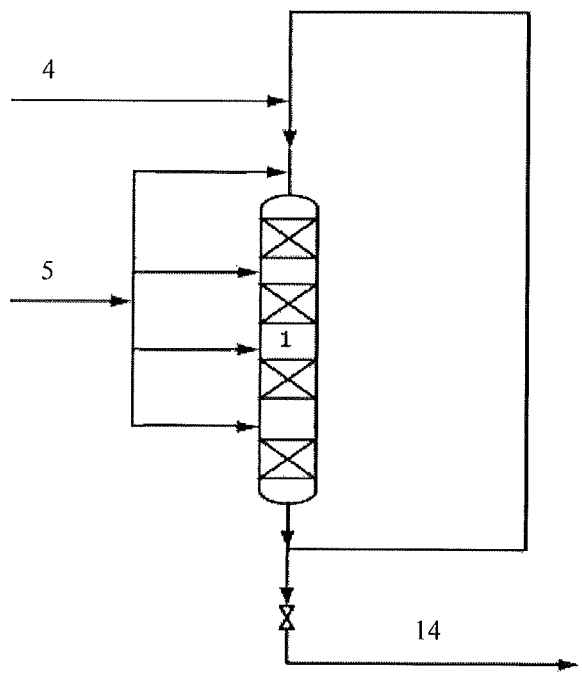

FIG. 1 schematically shows a technological process according to an example of the present invention. The present invention comprises a first reaction zone and a second reaction zone, each comprising two catalyst beds having catalysts thereon. In FIGS. 1 and 2, the reference sign 1 indicates the first reaction zone, 2 indicates the second reaction zone, 4 indicates a first stream containing benzene, and 5 indicates a first stream containing propylene.

A method for producing isopropyl benzene according to the present invention comprises the following steps.

Step A: the first stream containing benzene 4 and the first stream containing propylene 5 are let into the first reaction zone 1 to contact a first catalyst for alkylation, obtaining a first stream containing isopropyl benzene 12.

The first stream containing isopropyl benzene 12 is divided into two streams (stream 17 and stream 15). One stream (stream 17 which corresponds to stream Ia) circulates back to the first reaction zone 1 and the other stream (stream 15 which corresponds to stream IIa) enters into the second reaction zone 2.

The stream entering into the second reaction zone 2 contacts a second catalyst for alkylation, obtaining a second stream containing isopropyl benzene 13.

At least partial stream (stream 14 which corresponds to stream IIIa) of the second stream containing isopropyl benzene 13 is purified, obtaining the product isopropyl benzene.

The process as shown in FIG. 1 further comprises the step that a partial stream 18 (corresponding to stream IVa) of the second stream containing isopropyl benzene 13 circulates back to the second reaction zone 2. The process as shown in FIG. 1 can further comprises the step (not shown) of feeding a second stream containing benzene and/or a second stream containing propylene into the second reaction zone 2.

FIG. 2 shows a technological process in the prior art. Only one reactor 1 comprising four catalyst beds is arranged. The first stream containing propylene 5 is divided into four parts and enters into the four catalyst beds respectively. The first stream containing benzene 4 enters into the reactor from the top. The product stream is indicated by a reference sign 14.

Figure 3:
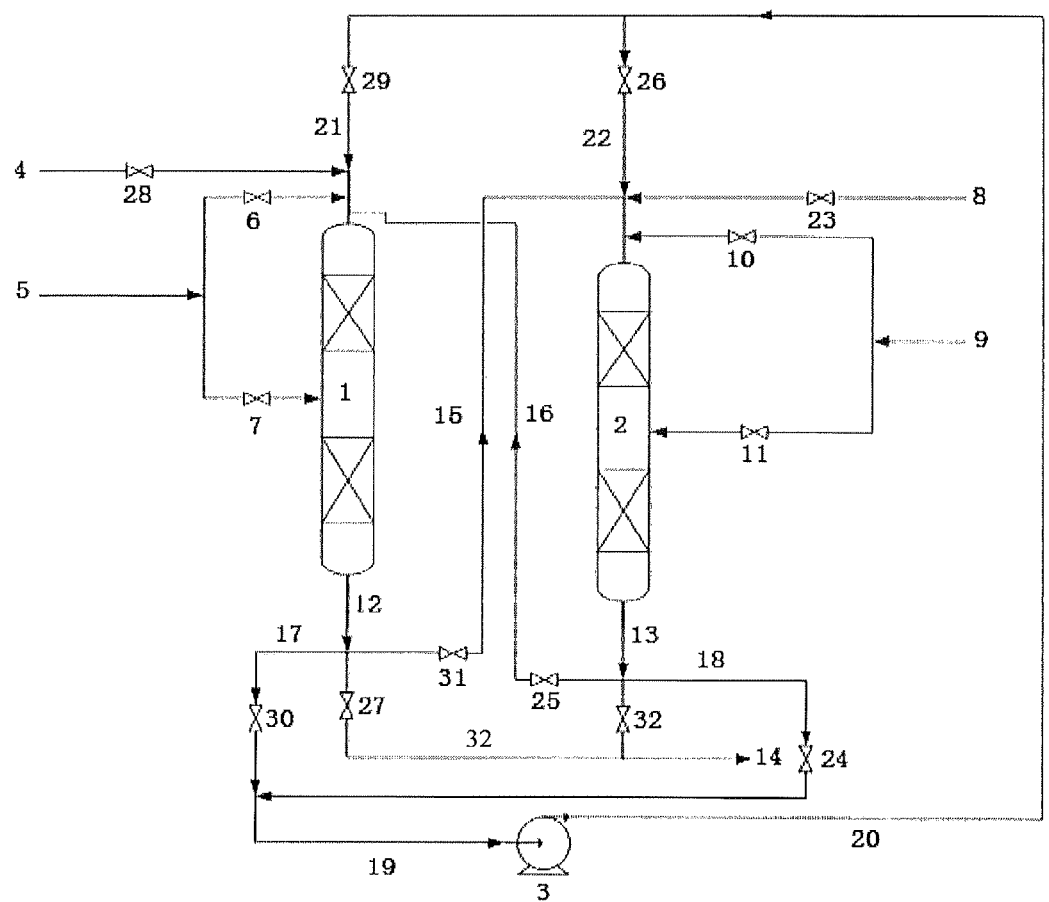
FIG. 3 shows a process flow diagram of an Example of the present invention.

FIG. 3 shows a technological flow according to an example of the present invention. When reaction begins, the first reaction zone (such as a reactor) is the primary reaction zone and the second reaction zone (such as a reactor) is the secondary reaction zone. Step A comprises the following sub steps. The first stream containing benzene 4 enters into the first reaction zone 1 from the top. The first stream containing propylene 5 enters into two catalyst beds respectively through a valve 6 and a valve 7 and reacts under the presence of the first catalyst, obtaining a stream 12 containing benzene, isopropyl benzene, poly-isopropyl benzene and traces of propylene. The stream 12 flowing out of the first reaction zone 1 is divided into two streams comprising a stream 17 (corresponding to stream Ia) which circulates back to the first reaction zone 1 through a circulating pump 3 and a stream 15 (corresponding to stream IIa) which directly enters into the second reaction zone 2. The stream entering the second reaction zone 2 contacts the second catalyst and continues to react, obtaining a second stream containing isopropyl benzene 13. Partial stream (stream 14 which corresponds to stream IIIa) of the second stream containing isopropyl benzene 13 is purified, obtaining the product isopropyl benzene. The above operations are carried out under the condition that valves 6, 7, 28, 29, 30, 31, and 32 are opened and valves 10, 11, 23, 24, 25, 26, and 27 are closed. The method further comprises circulating a partial stream 18 (corresponding to stream IVa) of the second stream containing isopropyl benzene 13 back to the second reaction zone 2 (for example, the stream 18 circulates back to the second reaction zone as a stream 22 passing through the valve 26 in step A. At this time, valve 24 and valve 26 are opened, but only allow very thin streams to pass through. The process as shown in FIG. 1 can further comprises feeding a second stream containing benzene 8 and/or a second stream containing propylene 9 into the second reaction zone 2. At this time, the valves 10, 11, and 23 are opened, but only allow very thin streams to pass through.

As the reaction proceeds to a certain phase, the activity of the first catalyst drops below a preset value (decreases or lost), the reaction switches from step A to step B. The two-reaction zone operating mode in step A is switched to a single-reaction zone operating mode in step B. The first stream containing benzene 4 and the first stream containing propylene 5 are turned off, such as by closing the valves 6, 7, and 28. Only the second stream containing benzene 8 and the second stream containing propylene 9 are let into the second reaction zone 2 to contact the second catalyst for alkylation, obtaining the second stream containing isopropyl benzene 13. The second stream containing isopropyl benzene 13 is divided into two streams. One stream (stream 18 corresponding to stream IVa) circulates back to the second reaction zone through valves 24 and 26 and the other stream (stream 14 corresponding to stream IIIa) is purified, obtaining the product isopropyl benzene. At this time, the valves 6, 7, 28, 25, 27, 29, 30, and 31 are closed, and the valves 10, 11, 23, 24, 26, and 32 are opened. At the same time, the deactivated catalyst in the first reaction zone is in an activity recovery phase, for example by regeneration or replacement.

When the activity of the first catalyst recovers, i.e., the regeneration or replacement of the deactivated catalyst is completed, the reaction proceeds from step B to step C. The single-reaction zone operating mode is switched to two-reaction zone operating mode. At this time point, the second reaction zone is the primary reaction zone and the first reaction zone is the secondary reaction zone. The second stream containing benzene 8 enters into the second reaction zone from the top. The second stream containing propylene 9 enters into the two catalyst beds respectively through valve 10 and valve 11 and contacts the second catalyst for reaction, obtaining stream 13 containing benzene, isopropyl benzene, and poly-isopropyl benzene. The stream 13 flowing out of the second reaction zone is divided into two streams comprising a stream 18 which circulates back to the second reaction zone through the circulating pump 3 as a stream 22 (corresponding to stream IVb) and a stream 16 (corresponding to stream IIIb) which directly enters into the first reaction zone for further reaction. The first stream containing isopropyl benzene 12 is obtained from the bottom of the first reaction zone. Partial stream of the first stream containing isopropyl benzene 12 flows through the valve 27 and enters into a phase of purification as a stream 32 (corresponding to stream IIb), obtaining isopropyl benzene. The above operations are carried out under the condition that valves 10, 11, 23, 24, 25 26, and 27 are opened and valves 6, 7, 28, 29, 30, 31, and 32 are closed. In an example of step C, a partial stream 17 of the first stream containing isopropyl benzene 12 circulates back to the first reaction zone 1 through a circulating pump as a stream 21 (corresponding to stream Ib). At this time, the valves 30 and 29 are opened, but only allow very thin streams to pass through. In another example of step C, the first stream containing benzene 4 and/or the first stream containing propylene 5 are let into the first reaction zone 1. At this time, the valves 6, 7, and 28 are opened, but only allow thin streams to pass through.

As the reaction proceeds to a certain phase, the activity of the second catalyst in the main reaction zone in step C drops below the preset value (activity decreases or lost). The reaction switches from two operating reaction zones in step C to single operating reaction zone in step D. The second stream containing benzene 8 and the second stream containing propylene 9 are turned off. Only the first stream containing benzene 4 and the first stream containing propylene 5 are let into the first reaction zone 1 and contact the first catalyst for alkylation, obtaining the first isopropyl containing stream 12. The first isopropyl containing stream 12 is divided into two streams. One stream (stream 17) circulates back to the first reaction zone through the circulating pump 3 as a stream 21 (corresponding to stream Ib). The other stream flows through the valve and enters into a phase of purification as a stream 32 (corresponding to stream IIb), obtaining the product isopropyl benzene. At the moment, the valves 6, 7, 28, 27, 29, and 30 are opened and the rest valves are closed. The catalyst in the second reaction zone is in a phase of activity recovery or replacement.

After the activity of the second catalyst in the second reaction zone recovers, i.e., the regeneration or replacement of the deactivated catalyst is completed, the reaction proceeds from step D to step A. The first reaction zone is the primary reaction zone and the second reaction zone is the secondary reaction zone. The single-reaction zone operating mode in step D is switched to a two-reaction zone operating mode in step A.

Example 1

The technology process as shown in FIG. 1 comprises two reactors, namely a first reactor and a second reactor. Each of the reactors comprises two catalyst beds. Each catalyst bed is loaded with 20 g MCM-56 zeolite catalyst.

The first reactor operates under the operating conditions including a reaction temperature in each of the catalyst beds of 125° C., a reaction pressure of 2.5 MPa, a flow of benzene of 135 g/h, a flow of propylene entering each of the catalyst beds of 20 g/h, a benzene to propylene ratio of 1.8, a weight hourly space velocity of propylene of 1.0 $hr^{-1}$, a circulating flow of 1050 g/h, and a recycle ratio of 6.

The second reactor operates under the operating conditions including a reaction temperature in each of the catalyst beds of 115° C., a reaction pressure of 2.5 MPa, a liquid phase space velocity of 4.4 $hr^{-1}$, and a recycle ratio of 0.

After continuously operating for 15 days, the reaction results including a 99.99% propylene conversion rate and 92 mg n-propyl benzene in 1 kg product isopropyl benzene are achieved.

Example 2

The technology process as shown in FIG. 1 comprises two reactors, namely the first reactor and the second reactor. Each of the first reactor and the second reactor comprises two catalyst beds. The first catalyst and the second catalyst are the same. Each of the catalyst beds is loaded with 10 g catalyst. The catalyst is prepared according to a method as disclosed in example 3 of literature CN 200410066636.2.

The operating conditions in the first reactor comprise a reaction temperature in each of the catalyst beds of 120° C., a reaction pressure of 2.5 MPa, a flow of benzene of 84 g/h, a flow of propylene entering each of the catalyst beds of 15 g/h, a benzene to propylene ratio of 1.5, a weight hourly space velocity of propylene of 1.5 hr$^{-1}$, a circulating flow of 798 g/h, and a recycle ratio of 7.0.

The operating conditions in the second reactor comprise a reaction temperature in each of the catalyst beds of 110° C., a reaction pressure of 2.5 MPa, a flow of propylene entering each of the catalyst beds of 0 g/h, a flow of benzene of 0 g/h, a liquid phase space velocity of 11 hr$^{-1}$, a circulating flow of 110 g/h, and a recycle ratio of 0.

After continuously operating for 15 days, the reaction results including a 99.99% propylene conversion rate and 87 mg n-propyl benzene in 1 kg product isopropyl benzene are achieved.

Example 3

The technology process as shown in FIG. 1 comprises two reactors, namely the first reactor and the second reactor. Each of the first reactor and the second reactor comprises three catalyst beds. The first catalyst and the second catalyst are the same. Each of the catalyst beds is loaded with 20 g catalyst. The catalyst is prepared according to a method as disclosed in example 3 of literature CN 200410066636.2.

The operating conditions in the first reactor comprise a reaction temperature in each of the catalyst beds of 135° C., the reaction pressure of 2.5 MPa, a flow of benzene of 220 g/h, a flow of propylene entering each of the catalyst beds of 20 g/h, a benzene to propylene ratio of 2.0, a weight hourly space velocity of propylene of 1.0 hr$^{-1}$, a circulating flow of 1692 g/h, and a recycle ratio of 6.

The second reactor operates under the following operating conditions: a reaction temperature in each of the catalyst beds of 105° C., a reaction pressure of 2.5 MPa, a flow of propylene in the first catalyst bed of 5 g/h and no propylene entering neither of the other two catalyst beds, a liquid phase space velocity of 4.8 hr$^{-1}$, a circulating flow of 340 g/h, and a recycle ratio of 1.2.

After continuously operating for 7 days, the reaction results including a 99.99% propylene conversion rate and 50 mg n-propyl benzene in 1 kg product isopropyl benzene are achieved.

Example 4

The technology process as shown in FIG. 1 comprises two reactors, namely the first reactor and the second reactor. Each of the first reactor and the second reactor comprises one catalyst bed. The first catalyst and the second catalyst are the same. Each catalyst bed is loaded with 20 g catalyst. The catalyst is prepared according to a method as disclosed in example 3 of literature CN 200410066636.2.

The first reactor operates under the operating conditions including a reaction temperature in the catalyst bed of 135° C., a reaction pressure of 3.0 MPa, a flow of benzene of 167 g/h, a flow of propylene entering the catalyst bed of 30 g/h, a benzene to propylene ratio of 3.0, a weight hourly space velocity of propylene of 1.5 hr$^{-1}$, a circulating flow of 2360 g/h, and a recycle ratio of 12.

The second reactor operates under the operating conditions including a reaction temperature in the catalyst bed of 110° C., a reaction pressure of 3.0 MPa, a liquid phase space velocity of 10 hr$^{-1}$, a circulating flow of 0 g/h, and a recycle ratio of 0.

After continuously operating for 15 days, the reaction results including a 99.99% propylene conversion rate and 110 mg n-propyl benzene in 1 kg product isopropyl benzene are achieved.

Example 5

The technology process as shown in FIG. 1 comprises two reactors, namely the first reactor and the second reactor. Each of the first reactor and the second reactor comprises two catalyst beds. Both the first catalyst and the second catalyst are MCM-56 zeolite. Each of the catalyst beds is loaded with 10 g catalyst.

The first reactor operates under the operating conditions including a reaction temperature in each of the catalyst beds of 110° C., a reaction pressure of 2.5 MPa, a flow of benzene of 279 g/h, a flow of propylene entering each of the catalyst beds of 30 g/h, a benzene to propylene ratio of 2.5, a weight hourly space velocity of propylene of 3.0 hr$^{-1}$, a circulating flow of 2700 g/h, and a recycle ratio of 8.0.

The second reactor operates under the operating conditions including a reaction temperature in each of the catalyst beds of 100° C., a reaction pressure of 2.5 MPa, a liquid phase space velocity of 17 hr$^{-1}$, a flow of benzene of 0 g/h, a flow of propylene entering each of the catalyst beds of 0 g/h, and a recycle ratio of 0.

After continuously operating for 7 days, the reaction results including a 99.99% propylene conversion rate and 75 mg n-propyl benzene in 1 kg product isopropyl benzene are achieved.

Example 6

The technology process as shown in FIG. 1 comprises two reactors, namely the first reactor and the second reactor. Each of the first reactor and the second reactor comprises two catalyst beds. The first catalyst and the second catalyst are the same. Each of the catalyst beds is loaded with 10 g catalyst. The catalyst is prepared according to a method as disclosed in example 2 of literature CN 200610029980.3.

The first reactor operates under the operating conditions including a reaction temperature in each of the catalyst beds of 115° C., a reaction pressure of 2.7 MPa, a flow of benzene of 75 g/h, a flow of propylene entering each of the catalyst beds of 8 g/h, a benzene to propylene ratio of 2.5, a weight hourly space velocity of propylene of 0.8 hr$^{-1}$, a circulating flow of 275 g/h, and a recycle ratio of 3.0.

The second reactor operates under the operating conditions including a reaction temperature in each of the catalyst beds of 120° C., a reaction pressure of 2.7 MPa, a flow of benzene of 75 g/h, a flow of propylene entering each of the catalyst beds of 0 g/h, a circulating flow of 91 g/h, a recycle ratio of 0.5, and a liquid phase space velocity of 9.1 hr$^{-1}$.

After continuously operating for 7 days, the reaction results including a 99.98% propylene conversion rate and 97 mg n-propyl benzene in 1 kg product isopropyl benzene are achieved.

Comparison Example 1

A technology process as shown in FIG. 2 comprises only one reaction zone (a reactor). The reactor comprises four catalyst beds. Propylene is divided into four parts and enters into the four catalyst beds respectively. Benzene enters into the reactor from the top. Each of the catalyst beds is loaded with 10 g preformed catalyst containing MCM-22 zeolite.

The reactor operates under the operating conditions including a reaction temperature in each of the catalyst beds of 140° C., a reaction pressure of 2.7 MPa, a flow of propylene entering each of the catalyst beds of 15 g/h, a flow of benzene of 178 g/h, a circulating flow of 1428 g/h, a benzene to propylene ratio of 1.6, s weight hourly space velocity of propylene of 1.5 $hr^{-1}$, and a recycle ratio of 6.0.

After continuously operating for 15 days, the reaction results including a 99.0% propylene conversion rate and 170 mg n-propyl benzene in 1 kg product isopropyl benzene are achieved. The results show that under the condition of low benzene to propylene ratio, the propylene conversion rate is relatively low and the content of n-propyl benzene is relatively high.

It can be learnt from the above results that under low benzene to propylene ratio in the prior art, the propylene conversion rate is relatively low and the content of n-propyl benzene is relatively high. However, according to the method of the present invention, high propylene conversion rate, long operating life of catalyst, and low n-propyl benzene content can be realized under even lower benzene to propylene ratio. The method of the present invention achieved better comprehensive results, thus having better economic and social benefits, as well as broader application prospect.

Example 7

A technology process as shown in FIG. 3 comprises a first reaction zone and a second reaction zone. Each of the First reaction zone and the second reaction zone comprises a reactor. Each reactor comprises two catalyst beds. Each of the catalyst beds is loaded with 10 g MCM-22 zeolite catalyst.

When reaction begins, the first reaction zone (reactor) is the primary reaction zone and the second reaction zone (reactor) is the secondary reaction zone. The valves 6, 7, 28, 29, 30, 31, and 32 are opened and the valves 10, 11, 23, 25, and 27 are closed. The valves 24 and 26 only allow small amount of the circulating stream to pass through. The first reactor operates under the operating conditions including a reaction temperature in each of the catalyst beds of 105° C., a reaction pressure of 2.5 MPa, a flow of propylene entering each of the catalyst beds of 10 g/h, flow of benzene of 75 g/h, a weight hourly space velocity of propylene of 1.0 $hr^{-1}$, a circulating flow of 475 g/h, and a recycle ratio of 5.0. The second reactor operates under the operating conditions including a reaction temperature in each of the catalyst beds of 125° C., a reaction pressure of 2.5 MPa, a flow of propylene entering each of the catalyst beds of 0 g/h, a flow of benzene of 0 g/h, a circulating flow of 95 g/h, a recycle ratio of 1.0, and a liquid phase space velocity of propylene of 9.5 $hr^{-1}$. After continuously operating for 30 days, the reaction results including a 99.95% propylene conversion rate at the outlet of the first reactor, a 99.99% propylene conversion rate at the outlet of the second reactor and 60 mg n-propyl benzene in 1 kg product isopropyl benzene at the outlet of the second reactor are achieved.

After continuously operating under the above conditions for 150 days, a 99.91% propylene conversion rate at the outlet of the first reactor and a 99.99% propylene conversion rate at the outlet of the second reactor are obtained. The two-reactor operating mode is switched to a single-reactor operating mode. The second reactor is in operation while the first reactor is in a phase of off-line catalyst activity recovery. The valves 6, 7, 25, 27, 28, 29, 30, and 31 are completely closed and allow no stream to pass through. In the meantime, the valves 10, 11, 23, 24, 26, and 32 are opened. The operating conditions in the second reactor at this moment include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 $hr^{-1}$, a circulating flow of 475 g/h, and a recycle ratio of 5.0. The reaction results include a 99.99% propylene conversion rate and 76 mg n-propyl benzene in 1 kg product isopropyl benzene.

After the catalyst regeneration in the first reactor is completed, the operation of a single reactor is switched back to the operation of both reactors. The first reactor after catalyst regeneration returns to the reaction system and becomes the secondary reactor; in the meantime, the second reactor remains to operate as the primary reactor. The valves 10, 11, 23, 24, 25, 26, and 27 are opened and the valves 6, 7, 28, 31, and 32 are closed. The valves 30 and 29 only allow small circulating stream to pass through. At this time, the operating conditions in the second reactor (the primary reactor) include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 $hr^{-1}$, a circulating flow of 475 g/h, and a recycle ratio of 5.0. The operating conditions in the first reactor (the secondary reactor) include a reaction temperature in each of the catalyst beds of 125° C., a reaction pressure of 2.5 MPa, a flow of propylene entering each of the catalyst beds of 0 g/h, a flow of benzene of 0 g/h, a circulating flow of 95 g/h, a recycle ratio of 1.0, and a liquid phase space velocity of propylene of 9.5 $hr^{-1}$.

After continuously operating for 30 days, the reaction results including a 99.96% propylene conversion rate at the outlet of the second reactor, a 99.99% propylene conversion rate at the outlet of the first reactor and 66 mg n-propyl benzene in 1 kg isopropyl benzene at the outlet of the first reactor are achieved.

Example 8

Example 8 is roughly the same as example 7; it is different from example 7 in the following aspects. In example 8, the catalyst is prepared according to a method disclosed in literature CN 200410066636.2. After the completion of catalyst regeneration in the first rector, the first reactor returns to the reaction system. The second reactor is the primary reactor and the first reactor is the secondary reactor. The valves 6 and 7 only allow small amount of stream to pass through. The second reactor operates under the operating conditions including a temperature in each of the catalyst beds of 125° C., a reaction pressure of 2.5 MPa, a flow of propylene entering each of the catalyst beds of 15 g/h, a flow of benzene of 105 g/h, a weight hourly space velocity of propylene of 1.5 $hr^{-1}$, a circulating flow of 800 g/h, and a recycle ratio of 5.9. The first reactor operates under the operating conditions including a temperature in each of the catalyst beds of 110° C., a reaction pressure of 2.5 MPa, a flow of propylene entering each of the catalyst beds of 2 g/h, a flow of benzene of 0 g/h, a circulating flow of 120 g/h, a recycle ratio of 0.9, and a liquid phase space velocity of 13 $hr^{-1}$. After continuously operating for 30 days, the reaction results including a 99.99% propylene conversion rate and 95 mg n-propyl benzene in 1 kg product isopropyl benzene are obtained.

Example 9

A technology process as shown in FIG. 3 comprises two reactors, each comprising three catalyst beds. Each of the catalyst beds is loaded with 10 g catalyst which is prepared according to the method disclosed in example 3 of literature CN200410066636.2.

When reaction begins, the valves 6, 7, 28, 29, 30, 31, and 32 are opened and the valves 10, 11, 25, and 27 are closed. The valves 23, 24, and 26 only allow small amount of circulating stream to pass through. The first reactor is the primary reactor and the second reactor is the secondary reactor. The first reactor operates under the operating condition including a reaction temperature in each of the catalyst beds of 95° C., a reaction pressure of 2.5 MPa, a flow of propylene entering each of the catalyst beds of 15 g/h, a flow of benzene of 210 g/h, a weight hourly space velocity of propylene of 1.5 hr$^{-1}$, a circulating flow of 1500 g/h, and a recycle ratio of 5.9. The second reactor operates under the operating condition including a reaction temperature in each of the catalyst beds of 110° C., a reaction pressure of 2.5 MPa, a flow of propylene entering the first catalyst bed of 5 g/h and no propylene stream entering the other two catalyst beds, a flow of benzene of 20 g/h, a circulating flow of 320 g/h, a recycle ratio of 1.1, and a liquid phase space velocity of 20 hr$^{-1}$. After continuously operating for 7 days, the reaction results including a 99.99% propylene conversion rate and 50 mg n-propyl benzene in 1 kg product isopropyl benzene are achieved.

After continuously operating under the above conditions for 150 days, a 99.91% propylene conversion rate at the outlet of the first reactor and a 99.99% propylene conversion rate at the outlet of the second reactor are obtained. The two-reactor operating mode is switched to a single-reactor operating mode. The second reactor is in operation while the first reactor is in a phase of off-line catalyst activity recovery. The valves 6, 7, 25, 27, 28, 29, 30, and 31 are completely closed and allow no stream to pass through. In the meantime, the valves 10, 11, 23, 24, 26, and 32 are opened. The operating conditions in the second reactor at this moment include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 hr$^{-1}$, a circulating flow of 475 g/h, and a recycle ratio of 5.0. The reaction results include a 99.99% propylene conversion rate and 76 mg n-propyl benzene in 1 kg product isopropyl benzene.

After the catalyst regeneration in the first reactor is completed, the operation of a single reactor is switched back to the operation of both reactors. The first reactor after catalyst regeneration returns to the reaction system and becomes the secondary reactor; in the meantime, the second reactor remains to operate as the primary reactor. The valves 10, 11, 23, 24, 25, 26, and 27 are opened and the valves 6, 7. 28, 31, and 32 are closed. The valves 30 and 29 only allow small circulating stream to pass through. At this time, the operating conditions in the second reactor (the primary reactor) include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 hr$^{-1}$, a circulating flow of 475 g/h, and a recycle ratio of 5.0. The operating conditions in the first reactor (the secondary reactor) include a reaction temperature in each of the catalyst beds of 125° C., a reaction pressure of 2.5 MPa, a flow of propylene entering each of the catalyst beds of 0 g/h, a flow of benzene of 0 g/h, a circulating flow of 95 g/h, a recycle ratio of 1.0, and a liquid phase space velocity of propylene of 9.5 hr$^{-1}$.

After continuously operating for 30 days, the reaction results including a 99.96% propylene conversion rate at the outlet of the second reactor, a 99.99% propylene conversion rate at the outlet of the first reactor and 66 mg n-propyl benzene in 1 kg product isopropyl benzene at the outlet of the first reactor are achieved.

Example 10

The technology process as shown in FIG. 3 comprises two reactors, each comprising only one catalyst bed. The catalyst bed of each reactor is loaded with 20 g catalyst. The catalyst is prepared according to the method disclosed in example 3 of literature CN 200410066636.2.

When reaction begins, the valves 6, 7, 28, 29, 30, 31, and 32 are opened and the valves 10, 11, 23, 24, 25, 26 and 27 are closed. The first reaction reactor is the primary reactor and the second reaction reactor is the secondary reactor. The first reactor operates under the operating conditions including a reaction temperature in each catalyst bed of 135° C., a reaction pressure of 3.0 MPa, a flow of propylene entering each catalyst bed of 60 g/h, a flow of benzene of 167 g/h, a weight hourly space velocity of propylene of 1.5 hr$^{-1}$, a circulating flow of 2360 g/h, and a recycle ratio of 10. The second reactor operates under the operating conditions including a reaction temperature in each catalyst bed of 110° C., a reaction pressure of 3.0 MPa, a flow of propylene entering the catalyst bed of 0 g/h, a flow of benzene of 0 g/h, a circulating flow of 0 g/h, a recycle ratio of 0, and a liquid phase space velocity of 5.6 hr$^{-1}$. After continuously operating for 15 days, the reaction results including a 99.99% propylene conversion rate and 105 mg n-propyl benzene in 1 kg product isopropyl benzene are achieved.

After continuously operating under the above conditions for 150 days, a 99.91% propylene conversion rate at the outlet of the first reactor and a 99.99% propylene conversion rate at the outlet of the second reactor are obtained. The two-reactor operating mode is switched to a single-reactor operating mode. The second reactor is in operation while the first reactor is in a phase of off-line catalyst activity recovery. The valves 6, 7, 25, 27, 28, 29, 30, and 31 are completely closed and allow no stream to pass through. In the meantime, the valves 10, 11, 23, 24, 26, and 32 are opened. The operating conditions in the second reactor at this moment include a reaction temperature in the catalyst bed of 135° C., a reaction pressure of 2.5 MPa, a flow of propylene entering the catalyst bed of 10 g/h, a flow of benzene of 75 g/h, a weight hourly space velocity of propylene of 1.0 hr$^{-1}$, a circulating flow of 475 g/h, and a recycle ratio of 5.0. The reaction results include a 99.99% propylene conversion rate and 76 mg n-propyl benzene in 1 kg product isopropyl benzene.

After the catalyst regeneration in the first reactor is completed, the operation of a single reactor is switched back to the operation of both reactors. The first reactor after catalyst regeneration returns to the reaction system and becomes the secondary reactor; in the meantime, the second reactor remains to operate as the primary reactor. The valves 10, 11, 23, 24, 25, 26, and 27 are opened and the valves 6, 7. 28, 31, and 32 are closed. The valves 30 and 29 only allow small circulating stream to pass through. At this time, the operating conditions in the second reactor (the primary reactor) include a reaction temperature in the catalyst bed of 135° C., a reaction pressure of 2.5 MPa, a flow of propylene entering the catalyst bed of 10 g/h, a flow of benzene of 75 g/h, a weight hourly space velocity of propylene of 1.0 hr$^{-1}$, a circulating flow of 475 g/h, and a recycle ratio of 5.0. The operating conditions in the first reactor (the secondary reactor) include a reaction temperature in the catalyst bed of 125° C., a reaction pressure of 2.5 MPa, a flow of propylene entering the catalyst bed of 0 g/h, a flow of benzene of 0 g/h, a circulating flow of 95 g/h, a recycle ratio of 1.0, and a liquid phase space velocity of 9.5 hr$^{-1}$.

After continuously operating for 30 days, the reaction results including a 99.96% propylene conversion rate at the outlet of the second reactor, a 99.99% propylene conversion rate at the outlet of the first reactor and 66 mg n-propyl benzene in 1 kg product isopropyl benzene at the outlet of the first reactor are achieved.

Example 11

The technology process as shown in FIG. 3 comprises two reactors, each comprising two catalyst beds. Each of the catalyst beds of each reactor is loaded with 30 g catalyst. The catalyst is prepared according to the method disclosed in example 3 of literature CN 200410066636.2.

When reaction begins, the valves 6, 7, 28, 29, 30, 31, and 32 are opened and the valves 10, 11, 23, 24, 25, 26 and 27 are closed. The first reaction reactor is the primary reactor and the second reaction reactor is the secondary reactor. The first reactor operates under the operating conditions including a reaction temperature in each of the catalyst beds of 125° C., a reaction pressure or 2.7 MPa, a flow of propylene entering each of the catalyst beds of 30 g/h, a flow of benzene of 178 g/h, a weight hourly space velocity of propylene of 1.0 hr$^{-1}$, a circulating flow of 1200 g/h, and a recycle ratio of 5.0. The second reactor operates under the operating conditions including a reaction temperature in each of the catalyst beds of 110° C., a reaction pressure of 2.7 MPa, a flow of propylene entering each of the catalyst beds of 0 g/h, a flow of benzene of 0 g/h, a circulating flow of 0 g/h, a recycle ratio of 0, and a liquid phase space velocity of 7.9 hr$^{-1}$. After continuously operating for 10 days, the reaction results including a 99.99% propylene conversion rate and 88 mg n-propyl benzene in 1 kg product isopropyl benzene are achieved.

After continuously operating under the above conditions for 150 days, a 99.91% propylene conversion rate at the outlet of the first reactor and a 99.99% propylene conversion rate at the outlet of the second reactor are obtained. The two-reactor operating mode is switched to a single-reactor operating mode. The second reactor is in operation while the first reactor is in a phase of off-line catalyst activity recovery. The valves 6, 7, 25, 27, 28, 29, 30, and 31 are completely closed and allow no stream to pass through. In the meantime, the valves 10, 11, 23, 24, 26, and 32 are opened. The operating conditions in the second reactor at this moment include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 hr$^{-1}$, a circulating flow of 475 g/h, and a recycle ratio of 5.0. The reaction results include a 99.99% propylene conversion rate and 76 mg n-propyl benzene in 1 kg product isopropyl benzene.

After the catalyst regeneration in the first reactor is completed, the operation of a single reactor is switched back to the operation of both reactors. The first reactor after catalyst regeneration returns to the reaction system and becomes the secondary reactor; in the meantime, the second reactor remains to operate as the primary reactor. The valves 10, 11, 23, 24, 25, 26, and 27 are opened and the valves 6, 7. 28, 31, and 32 are closed. The valves 30 and 29 only allow small circulating stream to pass through. At this time, the operating conditions in the second reactor (the primary reactor) include a reaction temperature in each of the catalyst beds of 135° C., a reaction pressure of 2.5 MPa, a flow of propylene entering each of the catalyst beds of 10 g/h, a flow of benzene of 75 g/h, a weight hourly space velocity of propylene of 1.0 hr$^{-1}$, a circulating flow of 475 g/h, and a recycle ratio of 5.0. The operating conditions in the first reactor (the secondary reactor) include a reaction temperature in each of the catalyst beds of 125° C., a reaction pressure of 2.5 MPa, a flow of propylene entering each of the catalyst beds of 0 g/h, a flow of benzene of 0 g/h, a circulating flow of 95 g/h, a recycle ratio of 1.0, and a liquid phase space velocity of 9.5 hr$^{-1}$.

After continuously operating for 30 days, the reaction results including a 99.96% propylene conversion rate at the outlet of the second reactor, a 99.99% propylene conversion rate at the outlet of the first reactor and 66 mg n-propyl benzene in 1 kg product isopropyl benzene at the outlet of the first reactor are achieved.

Example 12

Example 12 is roughly the same as example 7; it is different from example 7 in the following aspects. In example 12, each catalyst bed of each reactor is loaded with 10 g MCM-56 zeolite catalyst. After the catalyst regeneration in the first reactor is completed, the first reactor returns to the reaction system. The second reactor remains to operate as the primary reactor and the first reactor is the secondary reactor. The valve 6 only allows small stream to pass through and the valves 29 and 30 are closed. The second reactor operates under the operating conditions including a reaction temperature in each catalyst bed of 100° C., a reaction pressure of 2.5 MPa, a flow of propylene entering each catalyst bed of 30 g/h, a flow of benzene of 450 g/h, a weight hourly space velocity of propylene of 3.0 hr$^{-1}$, a circulating flow of 2550 g/h, and a recycle ratio of 5.0. The first reactor operates under the operating conditions including a reaction temperature in each catalyst bed of 110° C., a reaction pressure of 2.5 MPa, a flow of propylene entering the first catalyst bed of 2 g/h, a flow of propylene entering the second catalyst bed of 0 g/h, a circulating flow of 0 g/h, a recycle ratio of 0, and a liquid phase space velocity of 25 hr$^{-1}$. After continuously operating for 7 days, the reaction results including a 99.98% propylene conversion rate and 55 mg n-propyl benzene in 1 kg product isopropyl benzene are obtained.

Comparison Example 2

A technology process as shown in FIG. 2 comprises only one reactor. The reactor comprises four catalyst beds. Propylene is divided into four parts and respectively enters into the four catalyst beds. Benzene enters into the reactor from the top. Each catalyst bed is loaded with 10 g MCM-22 zeolite catalyst.

The operating conditions include a reaction temperature in each of the catalyst beds of 145° C., a reaction pressure of 2.7 MPa, a flow of propylene entering each of the catalyst beds of 20 g/h, a flow of benzene of 370 g/h, and a circulating flow of 700 g/h, After continuously operating for 90 days, the reaction results including a 99.91% propylene conversion rate and 220 mg n-propyl benzene in 1 kg product isopropyl benzene are obtained. The above results show that in the prior art, the propylene conversion rate can be high under relatively high reaction temperature. But at the same time, the content of impurity n-propyl benzene is also high.

Comparison Example 3

A technology process as shown in FIG. 2 comprises only one reactor. The reactor comprises four catalyst beds. Propylene is divided into four parts and respectively enters into the four catalyst beds. Benzene enters into the reactor from the top. Each catalyst bed is loaded with 10 g MCM-22 zeolite catalyst.

The operating conditions include a reaction temperature in each of the catalyst beds of 115° C., a reaction pressure of 2.5 MPa, a flow of propylene entering each of the catalyst beds of 10 g/h, a flow of benzene of 75 g/h, and a circulating flow of 570 g/h.

After continuously operating for 120 days, the reaction results including a 99.30% propylene conversion rate and 97 mg n-propyl benzene in 1 kg product isopropyl benzene are obtained. The above results show that in the prior art, the content of impurity n-propyl benzene can be low under relatively low reaction temperature. But at the same time, the propylene conversion rate can also be reduced.

It can be learnt from the above data comparison that the present invention can realize the objectives of high propylene conversion rate, long operating life of catalyst as well as low content of n-propyl benzene in the product under low benzene to propylene ratio and wider range of temperature adjustment. In the meantime, it is unnecessary to shut down the total reactor system for catalyst regeneration or replacement, thereby realizing continuous production of isopropyl benzene. The present invention achieved excellent comprehensive results and has favorable economic and social benefits. The application prospect of the present invention is broad.

It should be noted that the above embodiments are described only for better understanding, rather than restricting, the present invention. The present invention has been explained with reference to typical embodiments. The terms used to explain the present invention should be understood as descriptive and explanatory terms instead of definitive ones. Amendments can be made to the present invention without departing from the scope and spirit of the present invention. Although the description relates to specific method, material and embodiments, the present invention is not limited to the specific examples in the description. On the contrary, the present invention can be expanded to include other methods and applications having the same functions.

The invention claimed is:

1. A method for producing isopropyl benzene, comprising:
step A: feeding a first stream containing benzene and a first stream containing propylene into a first reaction zone to contact a first catalyst for alkylation, and obtaining a first stream containing isopropyl benzene from the first reaction zone,
dividing the first stream containing isopropyl benzene into a stream Ia and a stream IIa, the stream Ia circulating back into the first reaction zone and the stream IIa entering a second reaction zone,
feeding the stream IIa into the second reaction zone to contact a second catalyst for alkylation and obtaining a second stream containing isopropyl benzene from the second reaction zone,
obtaining a partial stream IIIa from the second stream containing isopropyl benzene,
purifying the partial stream IIIa and obtaining a product isopropyl benzene, and
optionally, circulating a partial stream IVa of the second stream containing isopropyl benzene to the second reaction zone, wherein a ratio of a recycle ratio of the second reaction zone to the recycle ratio of the first reaction zone is 0-0.2,
wherein operating conditions in the first reaction zone comprise: a molar ratio of the benzene in the first stream containing benzene to the propylene in the first stream containing propylene being 0.5:1-2.0:1, a weight hourly space velocity of the first stream containing propylene calculated by propylene being 0.1-10 hr$^{-1}$, a reaction temperature being 90-180° C., a reaction pressure being 1.0-4.0 MPa, and a recycle ratio being 1-50, and/or
operating conditions in the second reaction zone comprises: a reaction temperature being 80-160° C., a reaction pressure being 1.0-4.0 MPa, and a liquid phase weight hourly space velocity being 1-100 hr$^{-1}$, and
wherein a total propylene conversion is 99.99 wt % or greater.

2. The method according to claim 1, wherein the method comprises circulating the partial stream IVa of the second stream containing isopropyl benzene to the second reaction zone.

3. The method according to claim 1, wherein the recycle ratio of the section reaction zone is 0.1-10.

4. The method according to claim 1, wherein the method comprises feeding a second stream containing benzene and/or a second stream containing propylene into the second reaction zone.

5. The method according to claim 4, wherein a weight hourly space velocity of the second stream containing benzene calculated by benzene is 0.5-30 hr$^{-1}$, and/or a weight hourly space velocity of the second stream containing propylene calculated by propylene is 0.1-5 hr$^{-1}$.

6. The method according to claim 4, wherein the second stream containing propylene enters into the second reaction zone by stages.

7. The method according to claim 1, wherein the first catalyst and/or the second catalyst is/are selected from the group consisting of Beta zeolite, mordenite, and zeolite having MWW stratified structure.

8. The method according to claim 1, wherein the first stream containing propylene enters the first reaction zone by stages.

9. The method according to claim 1, wherein the first reaction zone comprises a plurality of reactors in parallel connection, and/or the second reaction zone comprises a plurality of reactors in parallel connection.

10. The method according to claim 1, further comprising:
switching from the step A to step B when an activity of the first catalyst in the first reaction zone below a preset value, wherein the step B comprises:
turning off the first stream containing benzene and the first stream containing propylene,
feeding only the second stream containing benzene and the second stream containing propylene into the second reaction zone to contact the second catalyst for alkylation, and obtaining the second stream containing isopropyl benzene, and dividing the second stream containing isopropyl benzene into a stream IIIa and a stream IVa, the stream IVa circulating back to the second reaction zone and the stream IIIa being purified, obtaining the product isopropyl benzene, the first catalyst at this moment is in an activity recovery phase;

switching from the step B to step C after the activity of the first catalyst recovers, wherein the step C comprises:

feeding the second stream containing benzene and the second stream containing propylene into the second reaction zone to contact the second catalyst for alkylation, and obtaining the second stream containing isopropyl benzene, dividing the second stream containing isopropyl benzene into a stream IIIb and a stream IVb, the stream IVb circulating back to the second reaction zone and the stream IIIb entering into the first reaction zone, having the stream entering the first reaction zone to contact the first catalyst for alkylation, and obtaining the first stream containing isopropyl benzene, purifying at least a partial stream IIb of the first stream containing isopropyl benzene and obtaining the product isopropyl benzene, and optionally, circulating a partial stream Ib of the first stream containing isopropyl benzene to the first reaction zone, wherein a ratio of a recycle ratio of the first reaction zone to that of the second reaction zone is 0-0.2;

switching from the step C to step D when an activity of the second catalyst in the second reaction zone drops below a preset value, wherein the step D comprises:

turning off the second stream containing benzene and the second stream containing propylene, feeding only the first stream containing benzene and the first stream containing propylene into the first reaction zone to contact the first catalyst for alkylation, obtaining the first stream containing isopropyl benzene, and dividing the first stream containing isopropyl benzene into a stream IIb and a stream Ib, the stream Ib circulating back to the first reaction zone and the stream IIb being purified, obtaining the product isopropyl benzene, the second catalyst at this moment being at an activity recovery phase; and switching from the step D to the step A after the activity of the second catalyst recovers.

11. The method according to claim 10, wherein in the step C, the operating conditions of the second reaction zone comprise: a molar ratio of the benzene in the second stream containing benzene to the propylene in the second stream containing propylene being 0.5:1-2.0:1, a weight hourly space velocity of the second stream containing propylene calculated by propylene being 0.1-10 $hr^{-1}$, a reaction temperature being 90-180° C., a reaction pressure being 1.0-4.0 MPa, and a recycle ratio being 1-50, and and/or the operating conditions in the first reaction zone comprises: a reaction temperature being 80-160° C., a reaction pressure being 1.0-4.0 MPa, and a liquid phase weight hourly space velocity being 1-100 $hr^{-1}$.

12. The method according to claim 10, wherein in the step C, the partial stream Ib of the first stream containing isopropyl benzene circulates to the first reaction zone.

13. The method according to claim 12, wherein in the step C, the recycle ratio of the first reaction zone is 0.1-10.

14. The method according to claim 10, wherein the step C comprises feeding the first stream containing benzene and/or the first stream containing propylene into the first reaction zone.

15. The method according to claim 14, wherein in the step C, the weight hourly space velocity of the first stream containing benzene calculated by benzene is 0.5-30 $hr^{-1}$ and that of the first stream containing propylene calculated by propylene is 0.1-5 $hr^{-1}$.

16. The method according to claim 1, comprising feeding into the secondary reaction zone, only the stream IIa and optionally the partial stream IVa of the second stream containing isopropyl benzene.

* * * * *